United States Patent
Puetz et al.

[11] Patent Number: 6,077,845
[45] Date of Patent: Jun. 20, 2000

[54] ACRIDIN DERIVATIVES

[75] Inventors: Claudia Katharina Puetz, Dueren; Wolfgang Werner Alfred Strassburger; Oswald Zimmer, both of Wuerselen; Werner Guenter Englberger, Stolberg, all of Germany

[73] Assignee: Gruenenthal GmbH, Aachen, Germany

[21] Appl. No.: 09/340,729

[22] Filed: Jun. 29, 1999

[30] Foreign Application Priority Data

Jul. 6, 1998 [DE] Germany .............................. 198 30 105

[51] Int. Cl.⁷ .................... A61K 31/473; C07D 219/06
[52] U.S. Cl. ............................................ 514/297; 546/104
[58] Field of Search ................... 514/297; 546/104

[56] References Cited

U.S. PATENT DOCUMENTS

| | | | |
|---|---|---|---|
| 3,652,589 | 3/1972 | Flick ................................. | 260/326.5 |
| 4,851,536 | 7/1989 | Skotnicki ............................ | 546/106 |
| 5,801,201 | 9/1998 | Graudums ........................... | 514/646 |
| 5,811,582 | 9/1998 | Buschmann ......................... | 564/355 |

FOREIGN PATENT DOCUMENTS

| | | |
|---|---|---|
| 780369 | 6/1997 | European Pat. Off. . |
| 799819 | 10/1997 | European Pat. Off. . |
| 864559 | 9/1998 | European Pat. Off. . |
| 922703 | 6/1999 | European Pat. Off. . |

OTHER PUBLICATIONS

Flick et al., "Studies on Chemical Structure and Analgetic Activity of Phenyl Substituted Aminomethylcyclohexanoles", *Arzneim. Forsch. Drug Res.* 28(1):107–13 (1978).

Mutschler, *Arzneimittel–Wirkungen*, Wissenschaftliche Verlagsgesellschaft, Stuttgart (1991) pp. 161–190.

*Primary Examiner*—Evelyn Mei Huang
*Attorney, Agent, or Firm*—Evenson, McKeown, Edwards & Lenahan, P.L.L.C.

[57] ABSTRACT

This invention relates to acridin derivatives of general formula

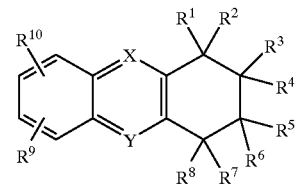

or pharmaceutically acceptable salts thereof, to a method of producing them and to their use as analgesics.

10 Claims, No Drawings

ACRIDIN DERIVATIVES

BACKGROUND OF THE INVENTION

This invention relates to acridin derivatives of general formula I

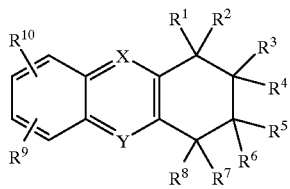

or pharmaceutically acceptable salts thereof, and relates to a method of producing them and to their use as drugs.

Classical opioids such as morphine are used for the therapy of severe and very severe pain. Their use is limited, however, by their known side effects, e.g. respiratory depression, vomiting, sedation and obstipation, and by the development of tolerance. Moreover, they are less effective for neuropathic or incidental pain, from which tumour patients suffer in particular.

Opioids develop their analgesic effect by binding to membrane receptors, which form part of the family of what are termed G protein-coupled receptors. The biochemical and pharmacological characterisation of subtypes of these receptors has shown that subtype-specific opioids exhibit a spectrum of effects and side-effects which is different to that of morphine for example. Whereas morphine binds selectively to what are termed $\mu$-receptors, endogenous enkephalins have been characterised as $\delta$-selective peptides. In the meantime, other pharmacological investigations have indicated that a plurality of subtypes of these opioid receptors ($\mu_1$, $\mu_2$, $\kappa_1$, $\kappa_2$, $\kappa_3$, $\delta_1$ and $\delta_2$) probably exist.

Knowledge of the physiological importance of $\delta$-receptor-selective substances has essentially been widened by the development of the non-peptidic antagonist naltrindol. In the meantime, it has been ascertained that $\delta$-agonists exhibit an autonomous antinociceptive potential. In addition to a multiplicity of experimental studies on animals, an investigation has also been performed in which the peptidic agonist D-alanine$^2$-D-leucine$^5$-enkephalin (DADL) was used on cancer patients on whom morphine no longer had an analgesic effect. When administered intrathecally, DADL exhibited a long-term analgesic effect. Moreover, $\delta$-agonists differ from $\mu$-agonists as regards their interaction with the "endogenous opioid antagonist" cholecystokinin (CCK).

SUMMARY OF THE INVENTION

The underlying object of the present invention was to provide substances having an analgesic effect which exhibit an affinity for $\delta$-opiate receptors.

This object has been achieved by the acridin derivatives according to the present invention. These new compounds exhibit a considerable affinity for $\delta$-opiate receptors.

The present invention relates to acridin derivatives corresponding to the general formula I:

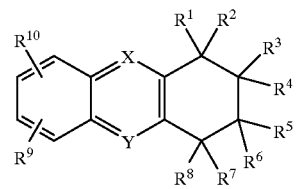

wherein
$R^1$ denotes A, if
$R^2$ denotes H or $OR^{12}$, or $R^2$ and $R^3$ form a double bond together,
$R^3$ denotes H, or $R^3$ and $R^2$ form a double bond together,
$R^4$ denotes $CH_2NR^{14}R^{15}$;
$R^5$ denotes H or $C_{1-6}$ alkyl;
$R^6$ denotes H or $C_{1-6}$ alkyl;
$R^7$ denotes H;
$R^8$ denotes H;
or
$R^3$ denotes A, if
$R^1$ denotes H or $R^1$ and $R^4$ form a double bond together;
$R^2$ denotes H;
$R^4$ denotes H or $OR^{12}$, or $R^4$ and $R^1$ form a double bond together or $R^4$ and $R^5$ form a double bond together;
$R^5$ denotes H, or $R^5$ and $R^4$ form a double bond together;
$R^6$ denotes $CH_2NR^{14}R^{15}$;
$R^7$ denotes H;
$R^8$ denotes H;
or
$R^5$ denotes A, if
$R^1$ denotes H;
$R^2$ denotes H;
$R^4$ denotes H;
$R^6$ denotes H or $OR^{12}$, or $R^6$ and $R^3$ form a double bond together, or $R^6$ and $R^7$ form a double bond together;
$R^7$ denotes H, or $R^7$ and $R^6$ form a double bond together;
$R^8$ denotes $CH_2NR^{14}R^{15}$;
and
A denotes

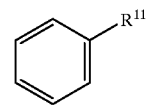

$R^9$ and $R^{10}$ are identical to or different from each other and denote H, OH, $C_{1-6}$ alkoxy, Cl, F, $CF_3$, CN, COOH, $CONR^{17}R^{18}$ or $COOR^{16}$;
$R^{11}$ denotes H, OH, $C_{1-6}$ alkoxy, O—$C_{3-7}$ cycloalkyl, O-aryl or O-heterocyclyl;
$R^{12}$ denotes H, $C_{1-6}$ alkyl, aryl or $COR^{13}$
$R^{13}$ denotes $C_{1-6}$ alkyl or aryl,
$R^{14}$, $R^{15}$ are identical to or different from each other and denote $C_{1-6}$alkyl, aryl or $C_{3-7}$-cycloalkyl;
$R^{16}$ denotes $C_{1-6}$ alkyl or aryl,
$R^{17}$, $R^{18}$ are identical to or different from each other and denote $C_{1-6}$ alkyl or aryl; and
X represents N if Y represents C, or X represents C if Y represents N,
or pharmaceutically acceptable salts thereof.

The preferred compounds of formula I are those in which $R^{14}$ and $R^{15}$ are identical to or different from each other and denote $C_{1-6}$ alkyl, and $R^1$ to $R^{13}$, $R^{16}$ to $R^{18}$, X and Y have the above meanings, or in which $R^{11}$ denotes OH or $C_{1-6}$ alkoxy, and $R^1$ to $R^{10}$, $R^{12}$ to $R^{18}$, X and Y have the above meanings, or in which $R^1$ denotes A, $R^{11}$ denotes OH or $C_{1-6}$ alkoxy, $R^{14}$ and $R^{15}$, independently of each other, denote $C_{1-6}$ alkyl, and $R^2$ to $R^{10}$, $R^{12}$, $R^{13}$, $R^{16}$ to $R^{18}$, X and Y have the above meanings, or in which $R^3$ denotes A, $R^{11}$ denotes OH or $C_{1-6}$ alkoxy, $R^{14}$ and $R^{15}$, independently of each other, denote $C_{1-6}$ alkyl, and $R^1$, $R^2$, $R^4$ to $R^{10}$, $R^{12}$, $R^{13}$, $R^{16}$ to $R^{18}$, X and Y have the above meanings, or in which $R^5$ denotes A, $R^{11}$ denotes OH or $C_{1-6}$ alkoxy, $R^{14}$ and $R^{15}$, independently of each other, denote $C_{1-6}$ alkyl, and $R^1$ to $R^4$, $R^6$ to $R^{10}$, $R^{12}$, $R^{13}$, $R^{16}$ to $R^{18}$, X and Y have the above meanings.

Other preferred compounds comprise the following:
rac-cis-[3-dimethylaminomethyl-2-(3-methoxyphenyl)]-1,2,3,4-tetrahydro-acridin-2-ol hydrochloride;
rac-cis-[4-dimethylaminomethyl-3-(3-methoxy-phenyl)]-1,2,3,4-tetrahydro-acridin-3-ol hydrochloride;
[3-dimethylaminomethyl-2-(3-hydroxy-phenyl)]-3,4-dihydro-acridin-1-ene hydrochloride;
rac-trans-[3-dimethylaminomethyl-2-(3-methoxy-phenyl)]-1,2,3,4-tetrahydro-acridin-2-ol hydrochloride;
rac-cis-[3-dimethylaminomethyl-2-(3-hydroxy-phenyl)]-1,2,3,4-tetrahydro-acridin-2-ol hydrochloride;
[1-(3-methoxy-phenyl)-3,4-dihydro-acridin-2-yl-methyl]-dimethylamine hydrochloride;
[3-(3-methoxy-phenyl)-1,2-dihydro-acridin-2-yl-methyl]-dimethylamine hydrochloride;
[3-dimethylaminomethyl-2-(3-methoxy-phenyl)]-3,4-dihydro-acridin-1-ene hydrochloride;
rac-trans-[1-(3-methoxy-phenyl)-1,2,3,4-tetrahydro-acridin-2-yl-methyl]-dimethylamine hydrochloride;
rac-cis-[1-(3-methoxy-phenyl)-1,2,3,4-tetrahydro-acridin-2-yl-methyl]-dimethylamine hydrochloride;
rac-trans-[3-(3-methoxy-phenyl)-1,2,3,4-tetrahydro-acridin-2-yl-methyl]-dimethylamine hydrochloride;
rac-cis-[3-(3-methoxy-phenyl)-1,2,3,4-tetrahydro-acridin-2-yl-methyl]-dimethylamine hydrochloride;
[3-(2-dimethylaminomethyl-3,4-dihydro-acridin-1-yl)]-phenol hydrochloride;
[3-(2-dimethylaminomethyl-1,2-dihydro-acridin-3-yl 1-phenol;
rac-trans-[3-(2-dimethylaminomethyl-1,2,3,4-tetra-hydro-acridin-3-yl)]-phenol;
rac-trans-[3-(2-dimethylaminomethyl-1,2,3,4-tetra-hydro-acridin-1-yl)]-phenol hydrochloride;
rac-cis-[2-dimethylaminomethyl-1-(3-methoxy-phenyl)]-3,3-dimethyl-1,2,3,4-tetrahydro-acridin-1-ol hydrochloride; and
3-(2-dimethylaminomethyl-3,3-dimethyl-3,4-dihydro-acridin-1-yl)-phenol hydrochloride.

In the context of the present invention, the expression "$C_{1-6}$ alkyl" means straight chain or branched hydrocarbons comprising 1 to 6 carbon atoms. Examples thereof include methyl, ethyl, propyl, isopropyl, n-butyl, sec-butyl, tert-butyl, neopentyl and n-hexyl.

In the context of the present invention, the expression "$C_{1-6}$ alkoxy" means straight chain or branched hydrocarbons comprising 1 to 6 carbon atoms, such as those defined above, which are bonded via an oxygen atom.

In the context of the present invention, the expression "$C_{3-7}$ cycloalkyl" means saturated cyclic hydrocarbons comprising 3 to 7 carbon atoms. Examples thereof include cyclopropyl, cyclobutyl, cyclopentyl, cyclohexyl or cycloheptyl.

In the context of the present invention, the expression "aryl" means phenyl groups which are unsubstituted or which are singly- or multiply-substituted with OH, F, Cl, $CF_3$, $C_{1-6}$ alkyl, $C_{1-6}$ alkoxy, $C_{3-7}$ cycloalkyl, $C_{2-6}$ alkylene, heterocyclyl or phenyl. This expression can also denote naphthyl.

In the context of the present invention, the expression "heterocyclyl" means 5- or 6-membered saturated or unsaturated heterocyclic compounds, which optionally comprise an aryl system which is incorporated by condensation, and which contain one or two hetero atoms from the group comprising nitrogen, oxygen and/or sulfur. Examples of saturated heterocycles include pyrolidine, pyrane, thiolane, piperidine and tetrahydrofliran. Examples of the unsaturated heterocyclic groups include thiophene, pyrrole, pyridine, pyrimidine, quinoline, isoquinoline, phthalazine and quinazoline.

These compounds are used as analgesics and are used quite generally for all pathological conditions which can usually be treated with δ-opiate receptors.

The present invention further relates to methods of producing compounds of formula I. In order to produce compounds of formula I, wherein derivatives are excluded in which the radicals have the following meanings, namely if $R^1$ denotes A, $R^2$ denotes H or $OR^{12}$ or if $R^2$ and $R^3$ form a double bond together, if $R^3$ denotes H or if $R^3$ and $R^2$ form a double bond together, if $R^4$ denotes $CH_2NR^{14}R^{15}$, if $R^5$ and $R^6$ denote $C_{1-6}$ alkyl, if $R^7$ and $R^8$ denote H, and if the $R^{11}$, $R^{12}$, $R^{14}$ and $R^{15}$ radicals have the same meaning as above, cyclohexane derivatives of general formulae II, III, or IV

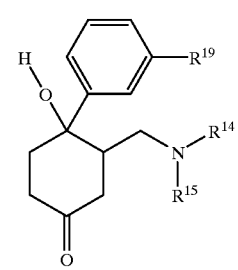

II

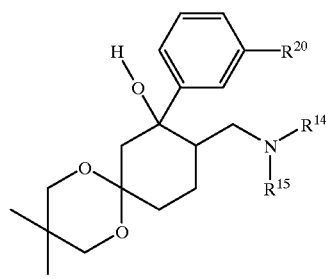

III

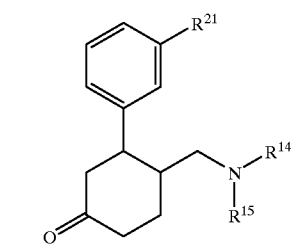

IV wherein
$R^{19}$, $R^{20}$ and $R^{21}$, independently of each other, represent H, $C_{1-6}$ alkoxy, O—$C_{3-7}$ cycloalkyl, O-aryl or O-heterocyclyl, and wherein $R^{14}$ and $R^{15}$ have the same meanings as above, are reacted with substituted 2-aminobenzaldehydes. These reactions are conducted in ethyl acetate or a $C_{1-4}$ alkyl alcohol in the presence of an acid, preferably from the group comprising hydrochloric acid, phosphoric acid or sulfuric acid, at temperatures between 20° C. and 80° C.

Elimination of the tertiary OH group and/or separation of the methyl ether grouping in the cyclization products obtained is effected by the reaction of the products with an acid, preferably from the group comprising formic acid, acetic acid, hydrobromic acid/glacial acetic acid, hydrobromic acid or methanesulfonic acid/methionine, at temperatures between 15° C. and 80° C.

Introduction of the $R^{12}$ radical, where $R^{12}$ does not represent hydrogen, is effected by the reaction of the corresponding cyclisation products with the relevant alkyl or aryl halides or with the relevant acid chlorides in the presence of a base such as potassium tertiary butylate for example, or with sodium hydride in an organic solvent e.g. dimethylformamide.

The synthesis of cyclohexanones of formula II, where $R^{14}$ and $R^{15}$ represent a methyl group, has already been described in DE-A 195 47 766.

Cyclohexanones of formula II, in which $R^{14}$ and $R^{15}$ do not represent a methyl group but otherwise have the same meaning as was explained in detail above, can be produced by the reaction of a 1,4-cyclohexanedione monoethylene ketal with immonium salts of formula V,

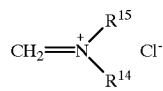

V followed by the reaction of the Mannich bases which are thus obtained with an organometallic compound of formula VI,

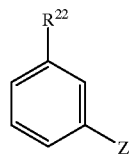

VI where Z denotes MgCl, MgBr, MgI or lithium and $R^{22}$ has the meaning as defined for $R^{11}$, and subsequent separation of the protective ketal group by an acid, for example hydrochloric acid.

The reaction of the Mannich bases with a Grignard compound of formula VI in which Z represents MgCl, MgBr or MgI, or with an organolithium compound of formula VI, can be conducted in an aliphatic ether, for example diethyl ether and/or tetrahydrofuran, at temperatures between −70° C. and 60° C. The reaction with a Grignard compound of formula VI can be effected with or without the addition of an entraining reagent, preferably 1,2-dibromoethane. Organolithium compounds of formula VI, in which Z denotes Cl, Br or I, can be obtained, for example, by reaction with a solution of n-butyl lithium in hexane by halogen-lithium exchange.

The separation of the methyl ether grouping in the cyclohexane derivatives which are obtained in this manner is effected by the reaction of these compounds with an acid, for example formic acid, acetic acid, hydrobromic acid/glacial acetic acid, hydrobromic acid or methanesulfonic acid/methionine at temperatures between 15° C. and 80° C.

Cyclohexane derivatives of formula III

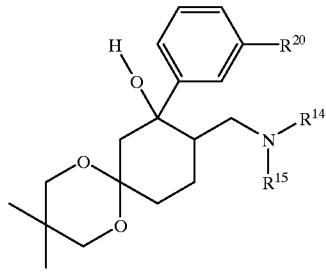

III can be obtained by the reaction of the Mannich base of formula VII,

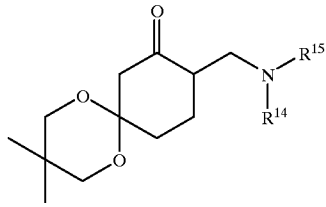

VII in which $R^{14}$ and $R^{15}$ have the same meanings as above, with an organometallic compound of formula VI, in which Z denotes MgCl, MgBr, MgI or lithium and $R^{22}$ has the meaning as defined for $R^{11}$.

The reaction of the Mannich base of formula VII with a Grignard compound of formula VI in which Z denotes MgCl, MgBr or MgI, or with an organolithium compound of formula VI, can be conducted in an aliphatic ether, for example diethyl ether and/or tetrahydrofuran, at temperatures between −70° C. and 60° C. The reaction with a Grignard compound of formula VI can be effected with or without the addition of an entraining reagent, preferably 1,2-dibromoethane. Organolithium compounds of formula VI, in which Z denotes Cl, Br or I, can be obtained, for example, by reaction with a solution of n-butyl lithium in hexane by halogen-lithium exchange.

The separation of the methyl ether grouping in the cyclohexane derivatives which are obtained in this manner is effected by the reaction of these compounds with an acid, for example formic acid, acetic acid, hydrobromic acid/glacial acetic acid, hydrobromic acid or methanesulfonic acid/methionine at temperatures between 15° C. and 80° C. Mannich bases of formula VII, wherein $R^{14}$ and $R^{15}$ represent a methyl group, have already been described in DE-A 195 25 137. Mannich bases of formula VII in which $R^{14}$ and $R^{15}$ do not represent a methyl group are obtained by the reaction of 3,3-dimethyl-1,5-dioxa-spiro[5.5]-undecan-8-one with immonium salts of formula V.

Cyclohexanones of formula IV

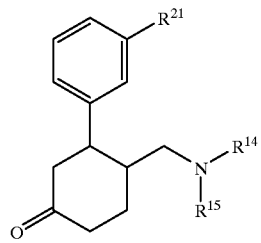

IV are obtained by the reaction of cyclohexane derivatives of formula III with acids, for example hydrochloric acid, formic acid or acetic acid. Subsequent hydrogenation of the products which are thus obtained using catalytically activated hydrogen, wherein platinum or palladium, absorbed on a support material such as activated carbon, are employed as the catalyst, results in compounds of formula IV. Hydrogenation is conducted in a solvent such as ethyl acetate or in a $C_{1-4}$ alkyl alcohol at pressures from 0.1 to 10 bar and temperatures of 20° C. to 80° C. Separation of the methyl ether group in compounds of formula IV is effected by reaction with hydrobromic acid or with hydrobromic acid/glacial acetic acid at temperatures between 20° C. and 80° C.

Acridin derivatives of general formula I, in which $R^1$ denotes A, $R^2$ denotes H or $OR^{12}$ or in which $R^2$ and $R^3$ form part of a double bond, $R^3$ denotes H or $R^3$ and $R^2$ form part of a double bond, $R^4$ denotes $CH_2NR^{14}R^{15}$, $R^5$ and $R^6$ denote $C_{1-6}$ alkyl, and $R^7$ and $R^8$ denote H, wherein the $R^{11}$, $R^{12}$, $R^{14}$ and $R^{15}$ radicals have the same meanings as above, are preferably produced by the reaction of 3,3-dialkyl-3,4-dihydro-2H-acridin-1-one derivatives [see W. Borsche et al., Justus Liebigs Ann. Chem. 550, 160, (1942)] with immonium chlorides of formula V at temperatures between 20° C. and 80° C. in a solvent, for example acetonitrile. The Mannich bases which result therefrom are reacted with an organometallic compound of formula VI in an aliphatic ether e.g. diethyl ether and/or tetrahydrofuran at temperatures between −70° C. and +60° C. The elimination of the tertiary OH group and/or the separation of the methyl ether group in the products which are obtained in this manner can be effected with formic acid, acetic acid, hydrobromic acid/glacial acetic acid, hydrobromic acid or methanesulfonic acid/methionine at temperatures between 20° C. and 100° C. Hydrogenation of the aliphatic double bond in these products by catalytically activated hydrogen, wherein platinum or palladium which is absorbed on a support material e.g. activated carbon can be employed as the catalyst, results in compounds of formula I according to the invention wherein $R^1$ denotes A, $R^2$ denotes H, $R^3$ denotes H, $R^4$ denotes $(CH_2)N(CH_3)_2$, $R^5$ denotes $CH_3$, $R^6$ denotes $CH_3$, and wherein $R^7$ and $R^8$ denote H. The reaction is conducted in a solvent such as acetic acid, ethyl acetate or a $C_{1-4}$ alkyl alcohol at pressures of 0.1 to 10 bar and at temperatures of 20° C. to 80° C.

Introduction of $R^{12}$ radicals, where $R^{12}$ does not represent hydrogen, is achieved by the reaction of the corresponding cyclisation products with the relevant alkyl or aryl halides or with the relevant acid chlorides in the presence of a base such as potassium tertiary butylate for example, or in the presence of sodium hydride in an organic solvent, preferably dimethylformamide.

The compounds of formula I can be converted in the known manner into their salts with physiologically compatible acids such as hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid. Salt formation is preferably conducted in a solvent such as diisopropyl ether, ethyl acetate, acetone and/or 2-butanone. Trimethylchlorosilane in aqueous solution is particularly suitable for the preparation of hydrochlorides.

δ-Opiate receptor binding investigations

Tests to determine the affinity of the compounds of formula I according to the invention for δ-opiate receptors were performed on meninx homogenates (homogenates of rat's brain, without the cerebellum and medulla oblongata, taken from male Wistar rats).

For this purpose, freshly prepared rat brains were each homogenised, while being cooled in ice, in 50 mmoles/l Tris-HCl (pH 7.4) and were centrifuged for 10 minutes at 5000 g and 40° C. After decantation and after rejecting the supernatant liquor, followed by renewed take-up and homogenization of the membrane sediment in 50 mmoles/l Tris-HCl (pH 7.4), the homogenate was subsequently centrifuged for 20 minutes at 20,000 g and 40° C. This washing step was repeated again. Thereafter, the supernatant liquor was decanted and the membrane sediment was homogenized in cold 50 mmoles/l Tris-HCl, 20% glycerol (w/v), 0.01% bacitracin (w/v) (pH 7.4) and aliquots thereof were frozen until required for testing. For the receptor binding tests, the aliquots were thawed and were diluted 1:10 with the binding test buffer. A solution of 50 μmoles/l Tris-HCl, 5 μmoles/l $MgCl_2$ (pH 7.4), supplemented by 0.1 (w/v) bovine serum albumin, was used as the buffer in the binding tests; 1 nmole/l [$^3$H]-2-D-Ala-deltorphin II was used as the radioactive ligand. The proportion of non-specific binding was determined in the presence of 10 μmoles/l naloxon.

In further batches, the compounds according to the invention were added in a series of concentrations and the displacement of the radioactive ligand from its specific binding site was determined. The batches concerned, which were each tested in triplicate, were incubated for 90 minutes at 37° C. and were subsequently harvested in order to determine the radioactive ligand which was bound to the membrane homogenate by filtration through a glass fibre filter (GF/B). The glass fiber filter discs were dried, and the radioactivity thereof was measured in a β-counter after adding a scintillator.

The affinity of the compounds according to the invention for the δ-opiate receptor was calculated as the $IC_{50}$ value according to the law of mass action, by means of nonlinear regression. $K_i$ values were calculated from the $IC_{50}$ values using the Cheng-Prussoff equation. The $K_i$ values in Table 1 are given as the mean value±standard deviation of three tests which were independent of each other.

TABLE 1

| Compound | δ-Opiate receptor binding $K_i$ (nM/l) |
| --- | --- |
| [1-(3-methoxy-phenyl)-3,4-dihydro-acridin-2-yl-methyl]-dimethylamine hydrochloride | 133 nM ± 15 nM |
| rac-trans-[1-(3-methoxy-phenyl)-1,2,3,4-tetrahydro-acridin-2-yl-methyl]-dimethylamine hydrochloride | 127 nM ± 12 nM |
| [3-(2-dimethylaminomethyl-3,4-dihydro-acridin-1-yl)]-phenol hydrochloride | 3.84 nM ± 1.59 nM |
| rac-trans-[3-(2-dimethylaminomethyl- | 4.17 nM ± 0.99 nM |

TABLE 1-continued

| Compound | δ-Opiate receptor binding $K_i$ (nM/l) |
|---|---|
| 1,2,3,4-tetrahydro-acridin-1-yl)]-phenol hydrochloride | |
| rac-cis-[2-dimethylaminomethyl-1-(3-methoxy-phenyl)]-3,3-dimethyl-1,2,3,4-tetrahydro-acridin-1-ol hydrochlorid | 60.2 nM ± 14.2 nM |
| 3-(2-dimethylaminomethyl-3,3-dimethyl-3,4-dihydro-acridin-1-yl)-phenol hydrochloride | 29.0 nM ± 3.4 nM |

EXAMPLES

In the following examples, the yields of the compounds prepared were not optimized. All temperatures are given as uncorrected values. Silica gel 60 (0.040–0.063 mm) supplied by E. Merck, Darmstadt, was used as the stationary phase for column chromatography. Thin layer chromatography investigations were performed using ready-to-use HPTLC plates made of silica gel 60 F 24 supplied by E. Merck, Darmstadt. The mixture ratios of the mobile phases for all the chromatography tests are always given in volume/volume. RT denotes room temperature; m.p. denotes melting point; the term "ether" denotes diethyl ether. Unless stated otherwise, petroleum ether with a boiling range of 50° C.–70° C. was used.

Example 1
rac-cis-[3-dimethylaminomethyl-2-(3-methoxy-phenyl)]-1,2,3,4-tetrahydro-acridin-2-ol hydrochloride and rac-cis-[4-dimethylaminomethyl-3-(3-methoxy-phenyl)]-1,2,3,4-tetrahydro-acridin-3-ol hydrochloride 4.8 g rac-cis-[3-dimethylaminomethyl-4-hydroxy-4-(3-methoxy-phenyl)]-cyclo-hexanone and 6.0 g 2-aminobenzaldehyde as the hydrochloride were dissolved at 20° C. under nitrogen in 200 ml methanol. The reaction mixture was subsequently heated to 80° C. and was treated at this temperature with 20 ml of 1 N hydrochloric acid. After a further 48 hours, the reaction solution was cooled to 0° C., treated with 200 ml ethyl acetate and made alkaline with saturated sodium hydroxide solution. The aqueous phase was extracted three times with 100 ml portions of ethyl acetate, the combined organic phases were dried over magnesium sulfate, and the mixture was concentrated under vacuum. The residue was purified by column chromatography using ethyl acetate/methanol in a ratio of 4/1 as the elutant. The first fraction contained 1.2 g rac-cis-[4-dimethylaminomethyl-3-(3-methoxy-phenyl)]-1,2,3,4-tetrahydro-acridin-3-ol base, as an amorphous beige solid. To prepare the hydrochloride, the solid was dissolved in 50 ml acetone while being heated, and was treated with an equimolar amount of trimethylchlorosilane and water. 1.0 g rac-cis-[4-di-methylaminomethyl-3-(3-methoxy-phenyl)]-1,2,3,4-tetra-hydro-acridin-3-ol hydrochloride (32% theoretical) was obtained in the form of white crystals.; m.p.: 175° C. to 180° C.

The second fraction yielded 2.0 g rac-cis-[3-dimethyl-aminomethyl-2-(3-methoxy-phenyl)]-1,2,3,4-tetrahydro-acridin-2-ol base, which was likewise obtained as an amorphous beige solid. Reaction of the solid with trimethylchlorosilane and water in equimolar amounts in 200 ml acetone gave 1.9 g (61.3% theoretical) rac-cis-[3-dimethylaminomethyl-2-(3-methoxy-phenyl)]-1,2,3,4-tetrahydro-acridin-2-ol hydrochloride in the form of white crystals (m.p.: 181° C. to 183° C.).

Example 2
rac-trans-[3-dimethylaminomethyl-2-(3-methoxy-phenyl)]-1,2,3,4-tetrahydro-acridin-2-ol hydrochloride and rac-cis-[3-dimethylaminomethyl-2-(3-hydroxy-phenyl)]-1,2,3,4-tetrahydro-acridin-2-ol hydrochloride Using the following cyclohexanones:
rac-trans-[3-dimethylaminomethyl-4-hydroxy-4-(3-methoxy-phenyl)]-cyclohexanone and
rac-cis-[3-dimethylaminomethyl-4-hydroxy-4-(3-methoxy-phenyl)]-cyclohexanone instead of rac-cis-[3-dimethylaminomethyl-4-hydroxy-4-(3-methoxy-phenyl)]-cyclo-hexanone as in Example 1, the following compounds were obtained by employing the procedure described in Example 1:
rac-trans-[3-dimethylaminomethyl-2-(3-methoxy-phenyl)]-1,2,3,4-tetrahydro-acridin-2-ol hydrochloride (m.p.: 186° C.–190° C.), and
rac-cis-[3-dimethylaminomethyl-2-(3-methoxy-phenyl)]-1,2,3,4-tetrahydro-acridin-2-ol hydrochloride (m.p.: >250° C.)

A compound analogous to rac-cis-[4-dimethylaminomethyl-3-(3-methoxy-phenyl)]-1,2,3,4-tetrahydro-acridin-3-ol hydrochloride was not obtained in either case.

Example 3
[3-dimethylaminomethyl-2-(3-hydroxy-phenyl)]-3,4-dihydro-acridin-1-ene hydrochloride and [3-dimethylaminomethyl-2-(3-methoxy-phenyl)]-3,4-dihydro-acridin-1-ene hydrochloride 3.65 g rac-cis-[3-dimethylaminomethyl-2-(3-methoxy-phenyl)]-1,2,3,4-tetrahydro-acridin-2-ol base were treated at room temperature with 20 ml methanesulfonic acid and 2.2 g methionine. The reaction mixture was stirred for three days at 20° C., the solution was evaporated to dryness under vacuum, the solid was dissolved in water, the solution was covered with ethyl acetate and the mixture was made alkaline with saturated sodium carbonate solution. The aqueous phase was extracted three times with 200 ml portions of ethyl acetate each time, and the combined organic phases were dried over magnesium sulfate and were freed from solvent under vacuum. The residue was purified by column chromatography using ethyl acetate/methanol in a ratio of 6/1 as the elutant. The first product fraction contained 0.3 g [3-dimethylaminomethyl-2-(3-methoxy-phenyl)]-3,4-dihydro-acridin-1-ene base. In order to prepare the hydrochloride, the amorphous solid was dissolved in 50 ml acetone and was treated with trimethylchlorosilane and water in equimolar amounts. 0.3 g (7.9% theoretical) of [3-dimethylaminomethyl-2-(3-methoxy-phenyl)]-3,4-dihydro-acridin-1-ene hydrochloride was obtained in the form of a beige, crystalline solid (m.p. 195° C.–197° C.). The second product fraction gave 2.2 g 3-dimethyl-aminomethyl-2-(3-hydroxy-phenyl)]-3,4-dihydro-acridin-1-ene base, which was converted into 2.1 g (57.5% theoretical) of the title compound [3-dimethylaminomethyl-2 -(3-hydroxyphenyl)]-3,4-dihydroacridin-1-ene hydrochloride (m.p.: 200° C. to 204° C.) by reaction with trimethyl-chlorosilane/water in equimolar amounts.

Example 4
[1-(3-methoxy-phenyl)-3,4-dihydro-acridin-2-yl-methyl]-dimethylamine hydrochloride and [3-(3-methoxy-phenyl)-1,2-dihydro-acridin-2-yl-methyl]-dimethylamine hydrochloride Step 1: rac-cis-[9-dimethylaminomethyl-8-(3-methoxy-phenyl)]-3,3-dimethyl-1,5-dioxa-spiro[5.5]undecan-8-ol 36 g magnesium turnings were suspended in 100 ml of absolute tetrahydrofuran while stirring and passing dry nitrogen over the suspension. 280 g m-bromoanisole, dissolved in 200 ml of absolute tetrahydrofuran, were subsequently added drop-wise at 60° C. After the addition of bromoanisole was complete, the reaction mixture was stirred for a further hour at 60° C. 244 g 9-di-methylaminomethyl-3,3-dimethyl-1,5-dioxa-spiro[5.5]undecan-8-one dissolved in 1000 ml of absolute tetrahydrofuran were subsequently added at 15° C. to 20° C. The reaction mixture was stirred overnight while being cooled in ice and was treated with 1000 ml of saturated ammonium chloride solution while being cooled in ice. The aqueous phase was extracted twice with 250 ml portions of ether each time. The combined organic phases were washed with saturated sodium-chloride solution and were dried over magnesium sulfate. After evaporating the solvent under vacuum, the residue was treated with petroleum ether until the title compound crystallized out. 150 g (41% theoretical) rac-cis-[9-dimethylaminomethyl-8-(3-methoxy-phenyl)]-3,3-dimethyl-1,5-dioxa-spiro[5.5]undecan-8-ol were obtained in the form of white crystals; m.p.: 91° C. to 93° C.

Step 2: [1-(3-methoxy-phenyl)-3,4-dihydro-acridin-2-yl-methyl]-dimethylamine hydrochloride and [3-(3-methoxy-phenyl)-1,2-dihydro-acridin-2-yl-methyl]-dimethylamine hydrochloride 18 g of the product from Step 1 were dissolved in 200 ml methanol under dry nitrogen. The reaction mixture was treated with 7.7 g 2-aminobenzaldehyde as the hydrochloride and was subsequently heated to 80° C. After adding 400 ml 1 N hydrochloric acid, the reaction solution was stirred for eight days at 80° C. After cooling to room temperature, the reaction mixture was diluted with 200 ml ethyl acetate and was made alkaline with concentrated sodium hydroxide solution while being cooled in ice. The aqueous phase was extracted three times with 100 ml portions of ethyl acetate each time, and the combined organic phases were dried over magnesium sulfate and evaporated to dryness under vacuum. The residue was eluted and purified by column chromatography on silica gel using ethyl acetate/methanol in a ratio of 4/1. The first product fraction contained 5.4 g [3-(3-methoxy-phenyl)-1,2-dihydro-acridin-2-yl-methyl]-dimethylamine base in the form of beige crystals. In order to prepare the hydrochloride, the solid was dissolved with heating in 200 ml acetone and was treated with trimethylchlorosilane and water in equimolar amounts. 5.2 g (28.3% theoretical) [3-(3-methoxy-phenyl)-1,2-dihydro-acridin-2-yl-methyl]-dimethyl-amine hydrochloride were obtained (light yellow crystals, m.p.: 201° C. to 204° C.). 4.4 g [1-(3-methoxy-phenyl)-3,4-dihydro-acridin-2-yl-methyl]-dimethylamine base in the form of a beige, amorphous solid was obtained as the second fraction. To release the hydrochloride, the solid was dissolved with heating in 200 ml acetone and was treated with trimethylchlorosilane and water in equimolar amounts. 4.2 g (22.90% theoretical) [1-(3-methoxy-phenyl)-3,4-di-hydro-acridin-2-yl-methyl]-dimethylamine hydrochloride were obtained in the form of light yellow crystals, m.p.: 195° C. to 198° C.

Example 5
[3-(2-dimethylaminomethyl-3,4-dihydro-acridin-1-yl)]-phenol hydrochloride 5.4 g [1-(3-methoxy-phenyl)-3,4-dihydro-acridin-2-yl-methyl]-dimethylamine base were treated at room temperature with 40 ml methanesulfonic acid and 5.4 g methionine. The reaction mixture was stirred for ten days at 20° C. and was evaporated to dryness under vacuum. The solid was dissolved in water, the solution was covered with ethyl acetate, and the mixture was made alkaline with saturated sodium carbonate solution. The aqueous phase was extracted three times with 200 ml portions of ethyl acetate each time, and the combined organic phases were dried over magnesium sulfate and evaporated to dryness under vacuum. 2.4 g [3-(2-dimethylaminomethyl-3,4-dihydro-acridin-1-yl)]-phenol base were obtained. Dissolution of the yellow, amorphous solid in acetone with heating, followed by treating the solution with trimethylchlorosilane and water in equimolar amounts, gave 2.3 g [3-(2-dimethylaminomethyl-3,4-dihydro-acridin-1-yl)]-phenol hydrochloride (48% theoretical) in the form of light yellow crystals. (m.p.: >250° C.).

Example 6
3-(2-dimethylaminomethyl-1,2-dihydro-acridin-3-yl]-phenol

Using [3-(3-methoxy-phenyl)-1,2-dihydro-acridin-2-yl-methyl]-dimethylamine instead of [1-(3-methoxy-phenyl)-3,4-dihydro-acridin-2-yl-methyl]-dimethylamine, the following compound was obtained corresponding to Example 5 using the procedure described therein:
[3-(2-dimethylaminomethyl-1,2-dihydro-acridin-3-yl]-phenol (m.p.: 202° C.–206° C.).

Example 7
rac-trans-[1-(3-methoxy-phenyl)-1,2,3,4-tetrahydro-acridin-2-yl-methyl]-dimethylamine hydrochloride and rac-trans-[3-(3-methoxy-phenyl)-1,2,3,4-tetra-hydro-acridin-2-yl-methyl]-dimethylamine hydrochloride Step 1: [4-dimethylaminomethyl-3-(3-methoxy-phenyl)]-cyclohex-2-en-one 56 g of the product from Step 1 of Example 4 was dissolved in 370 ml tetrahydrofuran with stirring and in a nitrogen atmosphere. A mixture of 150 ml concentrated hydrochloric acid and 150 ml water was added drop-wise thereto while cooling the mixture in ice. The reaction mixture was stirred for two days at room temperature, and was diluted with 200 ml ethyl acetate and made alkaline with saturated sodium hydroxide solution. The aqueous phase was extracted three times with 100 ml portions of ethyl acetate each time, and the combined organic phases were washed with saturated sodium chloride solution and dried over magnesium sulfate. The solvent was evaporated under vacuum. The residual oil was dissolved in 200 ml acetone and was treated with an equimolar amount of trimethylchlorosilane and water. 38.3 g of [4-dimethyl-aminomethyl-3-(3-methoxy-phenyl)]-cyclohex-2-en-one were obtained as the hydrochloride in the form light yellow crystals. To release the base, the solid was dissolved in water while cooling in ice, and the solution was covered with ethyl acetate and made alkaline with saturated sodium carbonate solution. The aqueous phase was extracted three times with 100 ml portions of ethyl acetate each time and was dried over magnesium sulfate. After evaporating the solvent under vacuum, 36 g (88.7% theoretical) of the title compound were obtained as a yellow oil.

Step 2: rac-[4-dimethylaminomethyl-3-(3-methoxy-phenyl)]-cyclohexanone 28.5 g of the product from Step 1 were dissolved in 250 ml absolute methanol. 2.8 g of palladium-carbon (10%) were added as a catalyst while stirring and while passing dry nitrogen over the batch. The batch was subsequently hydrogenated for five hours at a pressure of 0.2 bar and at a temperature of 20° C. After filtration, the solvent was evaporated under vacuum, and the residue was purified by column chromatography on silica gel using ethyl acetate/methanol/diisopropyl ether in a ratio of 4/1/5 as the elutant. 7.2 g (25.4% theoretical) of rac-cis-[4-dimethylaminomethyl-3-(3-methoxy-phenyl)]- cyclohexanone in the form of an oil was obtained as the first product fraction. The second product fraction gave 7.4 g (26.1% theoretical) of rac-trans-[4-dimethylaminomethyl-3-(3-methoxy-phenyl)]-cyclohexanone, likewise as an oil.

Step 3: rac-trans-[1-(3-methoxy-phenyl)-1,2,3,4-tetrahydro-acridin-2-yl-methyl]-dimethylamine hydrochloride and rac-trans[3-(3-methoxy-phenyl)-1,2,3,4-tetrahydro-acridin-2-yl-methyl]-dimethylamine hydrochloride 2.6 g rac-trans-[4-dimethylaminomethyl-3-(3-methoxy-phenyl)]-cyclohexanone were dissolved in 100 ml ethanol while stirring and passing dry nitrogen over the batch. The reaction mixture was treated with 3.2 g 2-aminobenzaldehyde as the hydrochloride and was heated to 80° C. 11 ml 1 N hydrochloric acid were added at this temperature, and the reaction solution was stirred for two days at 80° C. After cooling to room temperature, the reaction mixture was diluted with 100 ml ethyl acetate and was made alkaline, while being cooled in ice, with concentrated sodium hydroxide solution. The aqueous phase was extracted three times with 100 ml portions of ethyl acetate each time, and the combined organic phases were dried over magnesium sulfate. After removing the solvent under vacuum, the residue was purified by column chromatography on silica gel using ethyl acetate/methanol in a ratio of 4/1. The first product fraction contained 2.1 g rac-trans-[3-(3-methoxy-phenyl)-1,2,3,4-tetrahydro-acridin-2-yl-methyl]-dimethylamine base in the form of beige crystals, which were converted into 2 g (52.6% theoretical) of the title compound rac-trans-[1-(3-methoxy-phenyl)-1,2,3,4-tetrahydro-acridin-2-yl-methyl]-dimethylamine hydrochloride (light yellow crystals, m.p.: 184° C. to 187° C.) by treatment with trimethylchlorosilane/water in equimolar amounts. The second fraction contained 0.4 g rac-trans-[1-(3-methoxy-phenyl)-1,2,3,4-tetrahydro-acridin-2-yl-methyl]-dimethylamine base. To release the hydrochloride, the solid was dissolved, with heating, in 50 ml acetone and was treated with trimethylchlorosilane and water in equimolar amounts. 0.4 g (10.5% theoretical) of the hydrochloride rac-trans-[1-(3-methoxy-phenyl)-1,2,3,4-tetrahydro-acridin-2-yl-methyl]-dimethylamine hydrochloride were obtained in the form of light yellow crystals; m.p.: 167° C. to 170° C.

Example 8 rac-cis-[1-(3-methoxy-phenyl)-1,2,3,4-tetrahydro-acridin-2-yl-methyl]-dimethylamine hydrochloride and rac-cis-[3-(3-methoxy-phenyl)-1,2,3,4-tetrahydro-acridin-2-yl-methyl]-dimethylamine hydrochloride Using rac-cis-[1-(3-methoxy-phenyl)-1,2,3,4-tetrahydro-acridin-2-yl-methyl]-dimethylamine instead of rac-trans-[3-(3-methoxy-phenyl)-1,2,3,4-tetrahydro-acridin-2-yl-methyl]-dimethylamine as in Example 7, the following compounds were obtained by employing the procedure described in Example 7:
rac-cis-[1-(3-methoxy-phenyl)-1,2,3,4-tetrahydro-acridin-2-yl-methyl]-dimethylamine hydrochloride (m.p.: 118° C.–120° C.), and
rac-cis-[3-(3-methoxy-phenyl)-1,2,3,4-tetrahydro-acridin-2-yl-methyl]-dimethylamine hydrochloride (m.p.: 210° C.–213° C.).

Example 9 rac-trans-[3-(2-dimethylaminomethyl-1,2,3,4-tetrahydro-acridin-1-yl)]-phenol hydrochloride 1 g rac-trans-[1-(3-methoxy-phenyl)-1,2,3,4-tetrahydro-acridin-2-yl-methyl]-dimethylamine base was treated at room temperature with 8 ml methanesulfonic acid and 1 g methionine. The reaction mixture was stirred for ten days at 20° C., and was thereafter evaporated to dryness under vacuum. The solid was dissolved in water and the solution was covered with ethyl acetate and made alkaline with a saturated sodium carbonate solution. The aqueous phase was extracted three times with 200 ml ethyl acetate each time, and the combined organic phases were dried over magnesium sulfate and evaporated to dryness under vacuum. 0.5 g rac-trans-[3-(2-dimethylaminomethyl-1,2,3,4-tetrahydro-acridin-1-yl)]phenol base was obtained. Dissolution of the yellow, amorphous solid in acetone, with heating, and treatment with trimethylchlorosilane and water in equimolar amounts, gave 0.5 g (52% theoretical) of rac-trans-[3-(2-dimethyl-amino-methyl-1,2,3,4-tetrahydro-acridin-1-yl)]-phenol hydrochloride (light yellow crystals, m.p.: 240° C.).

Example 10 rac-trans-[3-(2-dimethylaminomethyl-1,2,3,4-tetrahydro-acridin-3-yl)]-phenol

Using rac-trans-[3-(3-methoxy-phenyl)-1,2,3,4-tetrahydro-acridin-2-yl-methyl]-dimethylamine instead of rac-trans-[1-(3-methoxy-phenyl)-1,2,3,4-tetrahydro-acridin-2-yl-methyl]-dimethylamine as in Example 9, the following compound was obtained by employing the procedure described in Example 9:
rac-trans-[3-(2-dimethylaminomethyl-1,2,3,4-tetrahydro-acridin-3-yl)]-phenol.

Example 11

3-(2-dimethylaminomethyl-3,3-dimethyl-3,4-dihydro-acridin-1-yl)-phenol hydrochloride Step 1: 2-dimethylaminomethyl-3,3-dimethyl-3,4-dihydro-2H-acridin-1-one A solution of 2.25 g 3,3-dimethyl-3,4-dihydro-2H-acridin-1-one [W. Borsche et al., Justus Liebigs Ann. Chem. 550, 160 (1942)] in 12 ml of dry acetonitrile was treated with 0.95 g N,N-dimethylmethylene-immonium chloride and with one drop of acetyl chloride, and the mixture was stirred for three days at 20° C. The batch was treated with 30 ml of distilled water and was extracted twice with ethyl acetate. The aqueous phase was made alkaline by adding solid potassium carbonate (pH~9) and was extracted three times with dichloromethane. The combined extracts were washed with saturated sodium chloride solution, and were dried over sodium sulfate and evaporated to dryness under vacuum. 0.92 g (32.5% theoretical) of the title compound remained in the form of a light yellow oil.

Step 2: rac-cis-[2-dimethylaminomethyl-1-(3-methoxy-phenyl)]-3,3-dimethyl-1,2,3,4-tetrahydro-acridin-1-ol A solution of 0.75 g 3-bromoanisole in 12 ml of dry tetrahydrofuran was treated drop-wise at –50° C., while stirring and passing dry nitrogen over the batch, with 2.5 ml of a 1.6 M solution of n-butyllithium in n-hexane. After the addition was complete, the batch was stirred for a further 30 minutes and a solution of 0.85 g of the product from Step 2 in 2 ml of dry tetrahydrofuran was added drop-wise. After a reaction time of two hours at –50° C., the batch was treated with 10% hydrochloric acid and was extracted twice with ethyl acetate. The hydrochloric acid phase was made alkaline with potassium carbonate and was extracted twice with dichloromethane. The combined organic phases were dried over sodium sulfate and were concentrated by evaporation under vacuum. The residue was purified by column chromatography on silica gel using ethyl acetate/methanol in a ratio of 9/1 as the elutant. 0.47 g (40% theoretical) of the title compound was obtained as a viscous mass.

Step 3: 3-(2-dimethylaminomethyl-3,3-dimethyl-3,4-dihydro-acridin-1-yl)-phenol hydrochloride A mixture of 0.39 g of the product from Step 2, 2 ml methanesulfonic acid and 0.227 g methionine was stirred for nine days at 20° C., and was then stirred for a further ten days at 40° C. The batch was subsequently treated with ice, was made alkaline with a saturated sodium hydrogen carbonate solution, and was extracted three times with ethyl acetate. The extracts were washed with a saturated sodium chloride solution, dried over sodium sulfate and substantially evaporated under vacuum. The solid which was precipitated upon treating the residue with n-hexane was separated and dried under vacuum. (yield: 0.26 g). The solid was dissolved, with heating, in a mixture of 12 ml acetone and 35 ml tetrahydrofuran and was converted into the hydrochloride using trimethylchlorosilane and water in equimolar amounts. 0.175 g (44.3% theoretical) of the title compound were obtained in the form of crystals which melted at 240° C. with decomposition.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. An acridin compound corresponding to formula I:

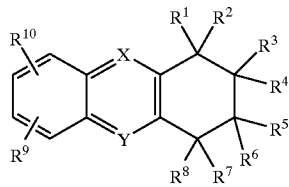

wherein $R^1$ denotes A, and $R^2$ denotes H or $OR^{12}$, or $R^2$ and $R^3$ together form a double bond, $R^3$ denotes H, or $R^3$ and $R^2$ together form a double bond, $R^4$ denotes $CH_2NR^{14}R^{15}$;

$R^5$ denotes H or $C_{1-6}$ alkyl;

$R^6$ denotes H or $C_{1-6}$ alkyl;

$R^7$ denotes H;

$R^8$ denotes H;

or $R^3$ denotes A, and $R^1$ denotes H or $R^1$ and $R^4$ form a double bond together;

$R^2$ denotes H;

$R^4$ denotes H or $OR^{12}$, or $R^4$ and $R^1$ form a double bond together or $R^4$ and $R^5$ form a double bond together;

$R^5$ denotes H, or $R^5$ and $R^4$ form a double bond together;

$R^6$ denotes $CH_2NR^{14}R^{15}$;

$R^7$ denotes H;

$R^8$ denotes H;

or $R^5$ denotes A, and $R^1$ denotes H;

$R^2$ denotes H;

$R^3$ denotes H, or $R^3$ and $R^6$ form a double bond together;

$R^4$ denotes H;

$R^6$ denotes H or $OR^{12}$, or $R^6$ and $R^3$ form a double bond together, or $R^6$ and $R^7$ form a double bond together;

$R^7$ denotes H, or $R^7$ and $R^6$ form a double bond together;

$R^8$ denotes $CH_2NR^{14}R^{15}$;

and

A denotes

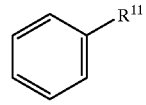

$R^9$ and $R^{10}$ are identical or different from each other and denote H, OH, $C_{1-6}$ alkoxy, Cl, F, $CF_3$, CN, COOH, $CONR^{17}R^{18}$ or $COOR^{16}$;

$R^{11}$ denotes H, OH, $C_{1-6}$ alkoxy, O—$C_{3-7}$ cycloalkyl, O-aryl or O-heterocyclyl;

$R^{12}$ denotes H, $C_{1-6}$ alkyl, aryl or $COR^{13}$ $R^{13}$ denotes $C_{1-6}$ alkyl or aryl, $R^{14}$, $R^{15}$ are identical or different from each other and denote $C_{1-6}$ alkyl, aryl or $C_{3-7}$-cycloalkyl;

$R^{16}$ denotes $C_{1-6}$ alkyl or aryl, $R^{17}$, $R^{18}$ are identical or different from each other and denote $C_{1-6}$ alkyl or aryl; and X represents N and Y represents CH, or X represents CH and Y represents N, or a pharmaceutically acceptable salt thereof.

2. A compound according to claim 1, wherein $R^{14}$ and $R^{15}$ are identical or different and denote $C_{1-6}$ alkyl.

3. A compound according to claim 1, wherein $R^{11}$ denotes OH or $C_{1-6}$ alkoxy.

4. A compound according to claim 1, wherein $R^1$ denotes A, $R^{11}$ denotes OH or $C_{1-6}$ alkoxy, and $R^{14}$ and $R^{15}$, independently of each other, denote $C_{1-6}$ alkyl.

5. A compound according to claim 1, wherein $R^3$ denotes A, $R^{11}$ denotes OH or $C_{1-6}$ alkoxy, and $R^{14}$ and $R^{15}$, independently of each other, denote $C_{1-6}$ alkyl.

6. A compound according to claim 1, wherein $R^5$ denotes A, $R^{11}$ denotes OH or $C_{1-6}$ alkoxy, and $R^{14}$ and $R^{15}$, independently of each other, denote $C_{1-6}$ alkyl.

7. A compound, selected from the group consisting of:

rac-cis-[3-dimethylaminomethyl-2-(3-methoxy-phenyl)]-1,2,3,4-tetrahydro-acridin-2-ol hydrochloride;

rac-cis-[4-dimethylaminomethyl-3-(3-methoxy-phenyl)]-1,2,3,4-tetrahydro-acridin-3-ol hydrochloride;

[3-dimethylaminomethyl-2-(3-hydroxy-phenyl)]-3,4-dihydro-acridin-1-ene hydrochloride;

rac-trans-[3-dimethylaminomethyl-2-(3-methoxyphenyl)]-1,2,3,4-tetrahydro-acridin-2-ol hydrochloride;

rac-cis-[3-dimethylaminomethyl-2-(3-hydroxyphenyl)]-1,2,3,4-tetrahydro-acridin-2-ol hydrochloride;

[1-(3-methoxy-phenyl)-3,4-dihydro-acridin-2-yl-methyl]-dimethylamine hydrochloride;

[3-(3-methoxy-phenyl)-1,2-dihydro-acridin-2-yl-methyl]-dimethylamine hydrochloride;

[3-dimethylaminomethyl-2-(3-methoxy-phenyl)]-3,4-dihydro-acridin-1-ene hydrochloride;

rac-trans-[1-(3-methoxy-phenyl)-1,2,3,4-tetrahydro-acridin-2-yl-methyl]-dimethylamine hydrochloride;

rac-cis-[1-(3-methoxy-phenyl)-1,2,3,4-tetrahydro-acridin-2-yl-methyl]-dimethylamine hydrochloride;

rac-trans-[3-(3-methoxy-phenyl)-1,2,3,4-tetrahydro-acridin-2-yl-methyl]-dimethylamine hydrochloride;

rac-cis-[3-(3-methoxy-phenyl)-1,2,3,4-tetrahydro-acridin-2-yl-methyl]-dimethylamine hydrochloride;

[3-(2-dimethylaminomethyl-3,4-dihydro-acridin-1-yl)]-phenol hydrochloride;

[3-(2-dimethylaminomethyl-1,2-dihydro-acridin-3-yl]-phenol;

rac-trans-[3-(2-dimethylaminomethyl-1,2,3,4-tetra-hydro-acridin-3-yl)]-phenol;

rac-trans-[3-(2-dimethylaminomethyl-1,2,3,4-tetra-hydro-acridin-1-yl)]-phenol hydrochloride;

rac-cis-[2-dimethylaminomethyl-1-(3-methoxy-phenyl]-3,3-dimethyl-1,2,3,4-tetrahydro-acridin-1-ol hydrochloride; and 3-(2-dimethylaminomethyl-3,3-dimethyl-3,4-dihydro-acridin-1-yl)-phenol hydrochloride.

8. A method of producing an acridin compound corresponding to formula I:

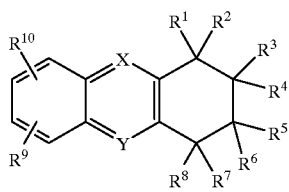

I wherein $R^1$ to $R^{10}$ have the meanings according to claim 1, wherein compounds are excluded in which $R^1$ denotes A, $R^2$ denotes H or $OR^{12}$, $R^3$ denotes H, or $R^3$ and $R^2$ form a double bond together, $R^4$ denotes $CH_2NR^{14}R^{15}$, $R^5$ and $R^6$ denote $C_{1-6}$ alkyl, $R^7$ and $R^8$ denote H, and $R^{11}$, $R^{12}$, $R^{14}$ and $R^{15}$ have the same meanings as in claim 1, said method comprising the step of reacting a cyclohexane compound corresponding to formula II, III, or IV

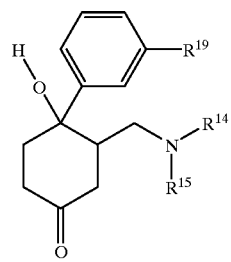

II

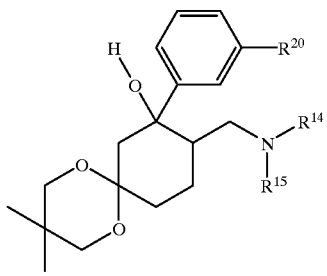

III

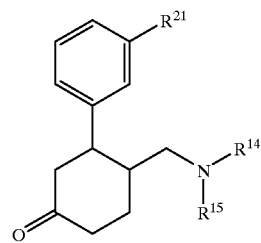

IV wherein $R^{19}$, $R^{20}$ and $R^{21}$, independently of each other, represent H, $C_{1-6}$ alkoxy, $O—C_{3-7}$-cycloalkyl, O-aryl or O-heterocyclyl, and wherein $R^{14}$ and $R^{15}$ have the same meanings as in claim 1, with a substituted 2-aminobenzaldehyde in a solvent selected from the group consisting of ethyl acetate and $C_{1-4}$ alkyl alcohols in the presence of an acid, and eliminating the tertiary OH group and/or cleaving the methyl ether group in the cyclization products obtained by reacting the products with an acid to form an acridin compound of formula I.

9. An analgesic pharmaceutical composition comprising an analgesically effective amount of an acridin compound of formula I according to claim 1, and at least one pharmaceutical carrier or adjuvant.

10. A method of alleviating pain in a patient in need thereof said method comprising the step of administering to said patient an analgesically effective amount of an acridin compound according to claim 1.

* * * * *